US011702390B2

(12) United States Patent
Iacono et al.

(10) Patent No.: US 11,702,390 B2
(45) Date of Patent: **\*Jul. 18, 2023**

(54) MECHANOCHEMICAL BASED SYNTHESIS OF PERFLUOROPYRIDINE MONOMERS FOR POLYMERIZATION

(71) Applicant: Government of the United States, as represented by the Secretary of the Air Force, Wright-Patterson AFB, OH (US)

(72) Inventors: Scott T. Iacono, Colorado Springs, CO (US); Chadron M. Friesen, Langley (CA)

(73) Assignee: United States of America as represented by the Secretary of the Air Force, Wright-Patterson AFB, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/075,018

(22) Filed: Dec. 5, 2022

(65) Prior Publication Data

US 2023/0121359 A1 Apr. 20, 2023

Related U.S. Application Data

(63) Continuation of application No. 17/493,024, filed on Oct. 4, 2021, now Pat. No. 11,603,357.

(51) Int. Cl.
| | | |
|---|---|---|
| C07D 213/61 | (2006.01) |
| C08G 73/06 | (2006.01) |
| C10G 71/00 | (2006.01) |
| C10M 147/04 | (2006.01) |
| C10M 169/04 | (2006.01) |
| C10N 50/08 | (2006.01) |

(52) U.S. Cl.
CPC ....... *C07D 213/61* (2013.01); *C08G 73/0627* (2013.01); *C10G 71/00* (2013.01); *C10M 147/04* (2013.01); *C10M 169/041* (2013.01); *C10M 2203/003* (2013.01); *C10M 2213/06* (2013.01); *C10N 2050/08* (2013.01)

(58) Field of Classification Search
CPC .. C07D 213/61; C08G 73/0627; C10G 71/00; C10M 147/04; C10M 169/041
See application file for complete search history.

(56) References Cited

U.S. PATENT DOCUMENTS

| | | | |
|---|---|---|---|
| 5,886,186 A | 3/1999 | Smith et al. |
| 2011/0015107 A1 | 1/2011 | Marchionni et al. |

OTHER PUBLICATIONS

Stewart, K. A.; Shuster, D; Leising, M,; Coolidge, I.; Lee, E.; Stevens, C.; Peloquin A. J.; Kure, D.; Abby R. Jennings, A. R.; Iacono, S. T.; "Synthesis, Characterization, and Thermal Properties of Fluoropyridyl-Functionalized Siloxanes of Diverse Polymeric Architectures." Macromolecules 2021, 54, 4871-4879.
Houck, M. B.; Brown, L. C.; Lambeth, R. H.; Iacono, S. T.; Exploiting the Site Selectivity of Perfluoropyridine for Facile Access to Densified Polyarylene Networks for Carbon-Rich Materials ACS Macro Lett. 2020, 9, 964-968.
Schumacher, C.; "N-(2,3,5,6-Tetrafluoropyridyl)sulfoximines: synthesis, X-ray crystallography, and halogen bonding" Organic Chemistry Frontiers 2020, vol. 7 Issue 23.
Titi, H. M. et al.; "Mechanochemistry for Synthesis" Angewandte Chemie, International Edition 2020, 59(3) 1018-1029.
Boswell, B. R.; Mansson, C. M. F.; Cox, J. M.; Jin, Z.; Romaniuk, J. H. A.; Lindquist, K. P.; Cegelski, L.; Xia, Y,; Lopez, S. A.; Burns, H. Z.; "Mechanochemical synthesis of an elusive fluorinated polyacetylene." Nature Chemistry 2002, 13, 41-46.
U.S. Appl. No. 17/493,024.

*Primary Examiner* — Vishal V Vasisth
(74) *Attorney, Agent, or Firm* — AFMCLO/JAZ; James F. McBride

(57) ABSTRACT

The present invention relates to a mechanochemical based synthesis of perfluoropyridine monomers, polymers made using such monomers and methods of making and using articles comprising such polymers. Such perfluoropyridine monomers are easily chemically tuned have the strength needed for high temperature applications and the flexibility needed for low temperature applications. In addition, to the aforementioned monomers, a mechanochemical based synthesis for such perfluoropyridine monomers is provided. All of the aforementioned performance application advantages are also found in polymers comprising Applicants' perfluoropyridine monomers.

7 Claims, No Drawings

MECHANOCHEMICAL BASED SYNTHESIS OF PERFLUOROPYRIDINE MONOMERS FOR POLYMERIZATION

CROSS-REFERENCE TO RELATED APPLICATION

The present application is a continuation of and claims priority to U.S. application Ser. No. 17/493,024 filed Oct. 4, 2021, now U.S. Pat. No. 11,603,357, the contents of which is hereby incorporated by reference in its entry.

RIGHTS OF THE GOVERNMENT

The invention described herein may be manufactured and used by or for the Government of the United States for all governmental purposes without the payment of any royalty.

FIELD OF THE INVENTION

The present invention relates to a mechanochemical based synthesis of perfluoropyridine monomers, polymers made using such monomers and methods of making and using articles comprising such polymers.

BACKGROUND OF THE INVENTION

The current plate of monomers used to produce polymers is limited. In particular, the plate of monomers used to make polymers for high temperature and low temperature applications is even more limited. Applicants' recognized that one of the reasons that many monomers cannot be used in such applications is they either have weak bonds and thus fail at high temperature applications and if they have strong bonds they are rigid and thus not suitable for low temperature applications. Based on such recognition, Applicants developed perfluoropyridine monomers. Such perfluoropyridine monomers comprise covalent fluorine-carbon bonds that provide the strength needed for high temperature applications and ether moieties that provide the flexibility needed for low temperature applications. In addition, surprisingly such ether moieties not only provide the desired low temperature flexibility but also provide backbone strength for the monomer via the ether's association with carbons in the monomer's backbone that further increases the strength needed for high temperature applications without detracting from low temperature flexibility. A further advantage of the disclosed perfluoropyridine monomers is that they can be easily chemically tuned for a specific application by pyridine positioning. All of the aforementioned performance application advantages are also found in polymers comprising Applicants' perfluoropyridine-containing monomers.

In addition, to the aforementioned perfluoropyridine monomers, Applicants disclose a mechanochemical based synthesis for such perfluoropyridine monomers. Such synthesis has a number of advantages including, but not limited to, no need for solvent, no need for a heat source to activate and maintain the reaction, synthesis flexibility as the synthesis can be run as a batch, semi-batch or continuous process and, while not being bound by theory, Applicants believe that the synthesis can be performed without the need for gravity.

SUMMARY OF THE INVENTION

The present invention relates to a mechanochemical based synthesis of perfluoropyridine monomers, polymers made using such monomers and methods of making and using articles comprising such polymers. Such perfluoropyridine-containing monomers are easily chemically tuned have the strength needed for high temperature applications and the flexibility needed for low temperature applications. In addition, to the aforementioned monomers, a mechanochemical based synthesis for such perfluoropyridine monomers is provided. All of the aforementioned performance application advantages are also found in polymers comprising Applicants' perfluoropyridine monomers.

Additional objects, advantages, and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

DETAILED DESCRIPTION OF THE INVENTION

Definitions

Unless specifically stated otherwise, as used herein, the terms "a", "an" and "the" mean "at least one".

As used herein, the terms "include", "includes" and "including" are meant to be non-limiting.

As used herein, the words "about," "approximately," or the like, when accompanying a numerical value, are to be construed as indicating a deviation as would be appreciated by one of ordinary skill in the art to operate satisfactorily for an intended purpose.

As used herein, the words "and/or" means, when referring to embodiments (for example an embodiment having elements A and/or B) that the embodiment may have element A alone, element B alone, or elements A and B taken together.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Monomers, Compositions Monomers and Articles Comprising Same

For purposes of this specification, headings are not considered paragraphs and thus this paragraph is paragraph fifteen of the present specification. The individual number of each paragraph above and below this paragraph can be determined by reference to this paragraph's number. In this paragraph fifteen, Applicants disclose a monomer having the following formula:

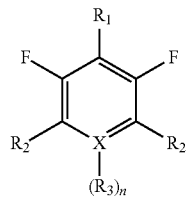

wherein
  a) $R_1$ is a branched unsubstituted hydrocarbon, branched unsubstituted hydrocarbon, branched substituted hydrocarbon or unbranched substituted hydrocarbon;
  b) each $R_2$ is independently fluorine, a branched unsubstituted hydrocarbon, branched unsubstituted hydrocarbon, branched substituted hydrocarbon or unbranched substituted hydrocarbon;
  c) X is nitrogen or carbon and when the indice n is 0, X is nitrogen and when X is carbon the indice n is 1; and
  d) when n is 1, $R_3$ is fluorine.

Applicants disclose the monomer according to paragraph fifteen of this specification wherein:
  a) for $R_1$ said branched unsubstituted hydrocarbon is an alkane, an alkene, an alkyne, or an aromatic;
  b) for $R_1$ said unbranched unsubstituted hydrocarbon is an alkane, an alkene, an alkyne, or an aromatic;
  c) for $R_1$ said branched substituted hydrocarbon comprises one or more Si, Ge, Sn, pnictogen, chalcogen and/or halogen substituents;
  d) for $R_1$ said unbranched substituted hydrocarbon comprises one or more Si, Ge, Sn, pnictogen, chalcogen and/or halogen substituents;
  e) for $R_2$ said branched unsubstituted hydrocarbon is an alkane, an alkene, an alkyne, or an aromatic;
  f) for $R_2$ said unbranched unsubstituted hydrocarbon is an alkane, an alkene, an alkyne, or an aromatic;
  g) for $R_2$ said branched substituted hydrocarbon comprises one or more Si, Ge, Sn, pnictogen, chalcogen and/or halogen substituents; and
  h) for $R_2$ said unbranched substituted hydrocarbon comprises one or more Si, Ge, Sn, pnictogen, chalcogen and/or halogen substituents.

Applicants disclose the monomer according to paragraph sixteen of this specification wherein:
  a) for $R_1$ said branched unsubstituted hydrocarbon is an alkane, an alkene, an alkyne, or an aromatic; preferably for $R_1$ said branched unsubstituted hydrocarbon is an alkene, an alkyne, or an aromatic, more preferably for $R_1$ said branched unsubstituted hydrocarbon is an aromatic;
  b) for $R_1$ said un branched unsubstituted hydrocarbon is an alkane, an alkene, an alkyne, or an aromatic; preferably for $R_1$ said unbranched unsubstituted hydrocarbon is an alkene, an alkyne, or an aromatic, more preferably for $R_1$ said unbranched unsubstituted hydrocarbon is an aromatic;
  c) for $R_1$ said branched substituted hydrocarbon comprises one or more Si, Ge, Sn, pnictogen, chalcogen and/or halogen substituents; preferably for $R_1$ said branched substituted hydrocarbon comprises one or more Si, N, P, O, S, Cl, Br, I and/or F substituents; more preferably for $R_1$ said branched substituted hydrocarbon comprises one or more N, O, I and/or F substituents; most preferably for $R_1$ said branched substituted hydrocarbon comprises one or more O and/or F substituents;
  d) for $R_1$ said unbranched substituted hydrocarbon comprises one or more Si, Ge, Sn, pnictogen, chalcogen and/or halogen substituents; preferably for $R_1$ said unbranched substituted hydrocarbon comprises one or more Si, N, P, O, S, Cl, Br, I and/or F; more preferably for $R_1$ said unbranched substituted hydrocarbon comprises one or more N, O, I and/or F substituents, most preferably for $R_1$ said branched substituted hydrocarbon comprises one or more O and/or F substituents;
  e) for $R_2$ said branched unsubstituted hydrocarbon is an alkane, an alkene, an alkyne, or an aromatic; preferably for $R_2$ said branched unsubstituted hydrocarbon is an alkene, an alkyne, or an aromatic, more preferably for $R_2$ said branched unsubstituted hydrocarbon is an aromatic;
  f) for $R_2$ said un branched unsubstituted hydrocarbon is an alkane, an alkene, an alkyne, or an aromatic; preferably for $R_2$ said unbranched unsubstituted hydrocarbon is an alkene, an alkyne, or an aromatic, more preferably for $R_2$ said unbranched unsubstituted hydrocarbon is an aromatic;
  g) for $R_2$ said branched substituted hydrocarbon comprises one or more Si, Ge, Sn, pnictogen, chalcogen and/or halogen substituents; preferably for $R_2$ said branched substituted hydrocarbon comprises one or more Si, N, P, O, S, Cl, Br, I and/or F substituents; more preferably for $R_2$ said branched substituted hydrocarbon comprises one or more N, O, I and/or F substituents; most preferably for $R_2$ said branched substituted hydrocarbon comprises one or more O and/or F substituents; and
  h) for $R_2$ said unbranched substituted hydrocarbon comprises one or more Si, Ge, Sn, pnictogen, chalcogen and/or halogen substituents; preferably for $R_1$ said unbranched substituted hydrocarbon comprises one or more Si, N, P, O, S, Cl, Br, I and/or F; more preferably for $R_2$ said unbranched substituted hydrocarbon comprises one or more N, O, I and/or F substituents, most preferably for $R_2$ said unbranched substituted hydrocarbon comprises one or more O and/or F substituents.

Applicants disclose the monomer according to paragraphs fifteen through seventeen of this specification wherein $R_1$ and each $R_2$ are independently a perfluoropolyalkylether (PFPAE), aryl or alkyl moiety.

Applicants disclose the monomer according to paragraphs fourteen through seventeen of this specification wherein $R_1$ and each $R_2$ each have a formula selected from Formulas 1 through 18 below:

Formula 1
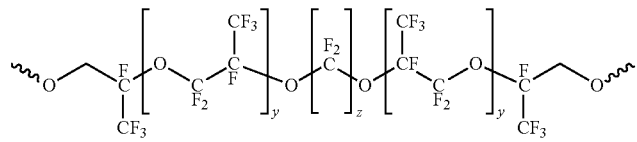
Formula 2
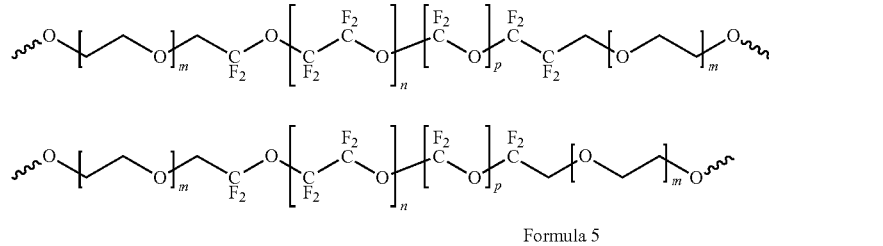
Formula 3
Formula 4
Formula 5
Formula 6
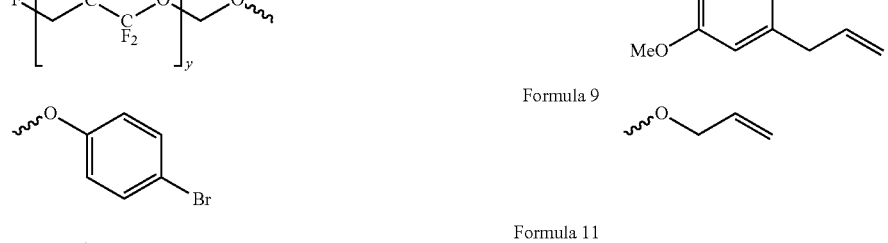
Formula 7
Formula 8
Formula 9
Formula 10
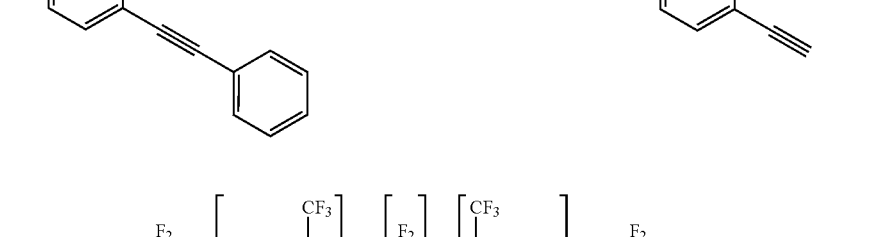
Formula 11
Formula 12
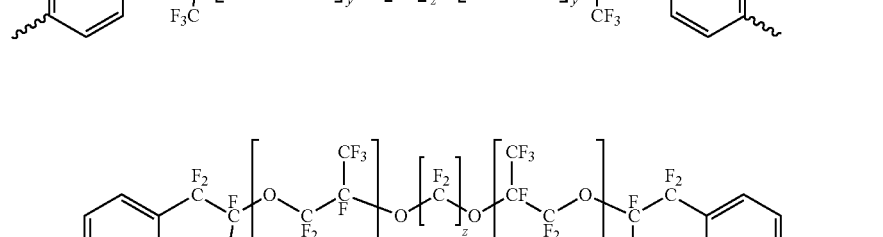
Formula 13
Formula 14

Formula 15

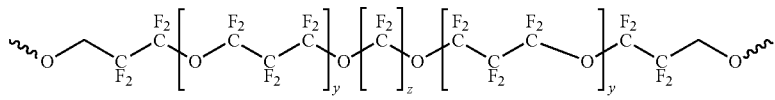

Formula 16

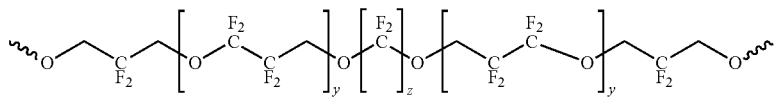

Formula 17

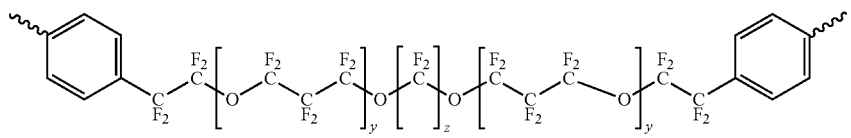

Formula 18

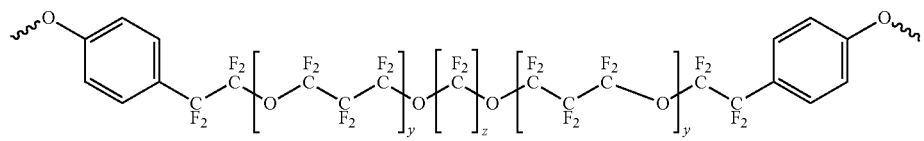

wherein the indices for said Formulas 1 through 18 are as follows:
a) the indice m is 0 to 100, preferably the indice m is 0 to 10, more preferably the indice m is 0 to 5; in one aspect m the indice m is 1 to 100;
b) the indice n' is 0 to 100, preferably the indice n is 1 to 50, more preferably the indice n is 1 to 10;
c) the indice p is 0 to 100, preferably the indice p is 1 to 50, more preferably the indice p is 1 to 10;
d) the indice y is 0 to 100, preferably the indice y is 1 to 50, more preferably the indice y is 1 to 10; and
e) the indice z is 1 to 6, preferably the indice z is 1 to 5, more preferably the indice z is 2 to 4.

Applicants disclose a composition comprising the monomer according to paragraphs fifteen through nineteen of this specification, said composition being a polymer network, a lubricant or an oxidizer.

Applicants disclose the composition of paragraph twenty of this specification, said composition being a polymer network.

Applicants disclose the composition of paragraph twenty of this specification, wherein said polymer network is a homopolymer network.

Applicants disclose an article comprising the polymer network according to paragraphs twenty through twenty-two of this specification, said article being a propellant binder, a deicing coating, a chemically protective coating, a friction reducing coating, gasket material or a separation membrane material.

Applicants disclose an article comprising the polymer network according to paragraphs twenty through twenty-two of this specification, said article being an aerospace vehicle, a motor vehicle, a separation unit or a consumer good. Non-limiting examples of aerospace vehicles are found in Table 1 below.

TABLE 1

Aerospace Vehicle Type and Modes of Guidance, Navigation, and Control

| Vehicle | GNC Methods | Maneuver Method |
|---|---|---|
| AIR | | |
| Weather Balloon | radiosonde, theodolite | pressure inside balloon |
| Manned aircraft | altimeter, inertial navigation system (INS), Global Positioning System (GPS) | thrust, flight control surfaces |
| Unmanned aircraft | altimeter, INS, GPS | thrust, flight control surfaces |
| Quadcopter | visual sensor, GPS | propeller(s) |
| Airborne Missile | altimeter, INS, GPS | thrust, flight control surfaces |
| AEROSPACE | | |
| Scientific Balloon | star camera, altimeter | pressure inside balloon |
| Sounding Rocket | ring laser gyro, altimeter, accelerometers | thrust, flight control surfaces |

TABLE 1-continued

Aerospace Vehicle Type and Modes of Guidance, Navigation, and Control

| Vehicle | GNC Methods | Maneuver Method |
|---|---|---|
| Space Shuttle | human-in-the-loop, star camera | thrust, flight control surfaces |
| Launch Vehicle (Rocket) | INS, ring laser gyro, altimeter, accelerometers | thrust, flight control surfaces |
| Ballistic Missile | INS, GPS | thrust, flight control surfaces |
| SPACE | | |
| Satellite | star camera, sun sensor, horizon sensor, GPS | thruster, electric propulsion, magnetorquer, momentum wheel |
| Space Station | human, star camera, sun sensor, horizon sensor, GPS | thruster, electric propulsion, magnetorquer, momentum wheel |
| Interplanetary Vehicle | star camera, sun sensor | thruster, electric propulsion, momentum wheel |

Examples of flight control surfaces include fins, ailerons, elevators and thrust includes the two-directional thrust force, as well as any gimbaled thrust vectoring the vehicle is capable of generating.

For generating monomers that have low glass transition temperatures, $R_1$ should be a PFPAE. This would also allow the monomer to be inserted into other materials such as bisphenol A and bisphenol AF, as examples, in order to enhance their temperature performance. Also, if $R_1$ is a PFPAE, and if 1,2-diphenylethyne or phenyl ethyne is inserted into the $R_2$ positions, this would afford thermoset polymers. In general, if the materials needs to be stiffer and stronger, a cross-linking monomer would be required, thus PFPAEs should be placed in both the $R_1$ and $R_2$ positions. If $R_1$ is aryls or alkyls then these materials can be radically polymerized through the alkene, reacted with thiols to form thiol-ene thermoset materials or polymerized with H-PDMS [poly (dimethylsiloxanes] or octadimethylhydrosilyl cubic siloxane (OctaSilane POSS) catalyzed with platinum, as examples. If aryls or alkyls are place in both $R_1$ and $R_2$ positon, then this provides for cross-linking capabilities, just like PFPAEs. There is also the opportunity for alkynes to thermally cure to form thermoset resins. Therefore, if aryl and alkyls are also inserted into the $R_2$ position, this provides cross-linking abilities.

Process of Making Monomers and Polymer Networks Comprising Same

Applicants disclose a process of making the monomer of paragraphs fifteen through nineteen of this specification, said process comprising:

a) combining a nucleophile, a carbonate and a fluoro-substituted aromatic in a mill to form a combined composition or combining a nucleophile, a carbonate and a fluoro-substituted aromatic to form a combined composition; and b) milling the said combined composition.

Applicants disclose the process according to paragraph twenty-six of this specification, wherein:

a) said nucleophile is selected from the group consisting of a tetrel, a pnictogen, a chalcogen and mixtures thereof, preferably said nucleophile is selected from the group consisting of a tetrel comprising carbon and/or silicon, a pnictogen comprising nitrogen, and/or phosphorus, a chalcogen comprising oxygen and/or sulfur and mixtures thereof, more preferably said nucleophile is selected from the group consisting of a tetrel comprising carbon, a pnictogen comprising nitrogen, a chalcogen comprising oxygen and mixtures thereof;

b) said carbonate is selected from the group consisting of potassium carbonate and cesium carbonate, preferably said carbonate comprises cesium carbonate; and c) said fluoro-substituted aromatic material is selected from the group consisting of a fluoro-substituted aromatic molecule, a polymer comprising a fluoro-substituted aromatic moiety and mixtures thereof, preferably said fluoro-substituted aromatic material is selected from the group consisting of perfluoropolyalkylether-, fluoro-silicon, and a polymer comprising a perfluroalkyl moiety, more preferably said fluoro-substituted aromatic material comprises perfluoropolyalkylethers.

Applicants disclose the process according to paragraphs twenty-six through twenty-seven of this specification, wherein said milling is conducted using a ball mill, a planetary ball mill, vibration ball mill, a stirring ball mill, a pin ball mill, a rolling ball mill, or an auger mill, preferably said milling is conducted using a ball mill.

Applicants disclose a process of making the polymer network according to paragraphs twenty through twenty-two of this specification, said process comprising combining a nucleophile and a monomer as detailed in to paragraphs fifteen to nineteen of this specification in a mill to form a combined composition or combining a nucleophile and a monomer according to paragraphs twenty through twenty-two of this specification to form a combined composition and then placing said combined composition in a mill and milling the said combined composition.

Applicants disclose the process of paragraph twenty-eight of this specification wherein nucleophile is selected from the group consisting of nucleophile is selected from the group consisting of a tetrel, a pnictogen, a chalcogen and mixtures thereof, preferably said nucleophile is selected from the group consisting of a tetrel comprising carbon and/or silicon, a pnictogen comprising nitrogen, and/or phosphorus, a chalcogen comprising oxygen and/or sulfur and mixtures thereof, more preferably said nucleophile is selected from the group consisting of a tetrel comprising carbon, a pnictogen comprising nitrogen, a chalcogen comprising oxygen and mixtures thereof.

Applicants disclose the process of paragraph twenty-nine of this specification wherein a second monomer other than a monomer according to paragraph fifteen of this specification is added to said ball mill during said process, preferably said second monomer is added after said combined composition is formed.

Materials that are needed to produce the monomers disclosed and/or claimed by Applicants in this specification can be purchased from companies such as: (Oakwood chemicals 730 Columbia Hwy. N, Estill, S.C. 29918); 4-bromophenol, 1,1,1-tris(4-hydroxylphenyl) ethane (TCI America 9211 North Harborgate Street Portland, Oreg. 97203); polyethylene glycol (PEG-200), bisphenol A, bisphenol AF, eugenol, allyl alcohol, potassium fluoride, calcium carbonate, lithium carbonate, potassium carbonate, and cesium carbonate (Alfa-Aesar, 2 Radcliff Rd, Tewksbury, Mass. 01876); diethylether; 2H,3H-perfluoropentane (Vertrel™ Chemours, The Chemours Company, 1007 Market Street P.O. Box 2047, Wilmington, Del. 19899); perfluoropyridine (SynQuest, SynQuest Laboratories, Inc., 13201 Rachael Blvd, Rt 2054, Alachua Fla. 32615); L-9939 perfluoropolyether diol (MACH I Inc., 340 E Church Rd, King of Prussia, Pa. 19406); Krytox® methylene alcohol (Chemours, The Chemours Company, 1007 Market Street P.O. Box 2047, Wilmington, Del. 19899).

EXAMPLES

The following examples illustrate particular properties and advantages of some of the embodiments of the present invention. Furthermore, these are examples of reduction to practice of the present invention and confirmation that the principles described in the present invention are therefore valid but should not be construed as in any way limiting the scope of the invention.

Example 1: Cesium carbonate (0.3495 g, 1.1 mmol), p-bromophenol (0.1909 g 1.1 mmol), and pentafluoropyridine (0.2721 g. 1.6 mmol) was added to the capsule and agitated for 20 minutes. GC results: retention time (%) 9.780 min (97.9%) mono, 15.439 min (1.6%) di.

Example 2: Cesium carbonate (0.3412 g, 1.0 mmol), p-bromophenol (0.1910 g 1.1 mmol), and pentafluoropyridine (0.2759 g. 1.6 mmol) was added to the capsule and agitated for 1 minute. GC results: retention time (%) 7.742 min (1.3%) Br-PhOH, 9.766 min (98.4%) mono, 15.428 min (0.3%) di.

Example 3: Cesium carbonate (0.3600 g, 1.1 mmol), p-bromophenol (0.4051 g 2.3 mmol), and pentafluoropyridine (0.1844 g. 1.1 mmol) was added to the capsule and agitated for 1 minute. GC results: retention time (%) 7.728 min (41.8%) Br-PhOH, 9.742 min (57.2%) mono, 15.412 (1.0%) di.

Example 4: Potassium carbonate (0.1586 g, 1.1 mmol), p-bromophenol (0.2016 g 1.2 mmol), and pentafluoropyridine (0.2875 g. 1.7 mmol) was added to the capsule and agitated for 1 minute. GC results: retention time (%) 7.743 min (92.5%) Br-PhOH, 9.753 min (7.522%) mono.

Example 5: This is a comparative example. Lithium carbonate (0.0807 g, 1.1 mmol), p-bromophenol (0.2215 g 1.3 mmol), and pentafluoropyridine (0.2853 g. 1.7 mmol) was added to the capsule and agitated for 1 minute. No reaction. GC results: retention time (%) 7.719 min (100%) Br-PhOH.

Example 6: This is a comparative example. Celite 545 (0.0863 g), p-bromophenol (0.1851 g), and pentafluoropyridine (0.2814 g. 1.7 mmol) was added to the capsule and agitated for 1 minute. No reaction. GC results: retention time (%) 7.719 min (100%) Br-PhOH.

Example 7: This is a comparative example. Silica (0.0898 g), p-bromophenol (0.2128 g), and pentafluoropyridine (0.2899 g. 1.7 mmol) was added to the capsule and agitated for 1 minute. No reaction. GC results: retention time (%) 7.719 min (100%) Br-PhOH.

Example 8: This is a comparative example. Calcium carbonate (0.1180 g, 1.2 mmol), p-bromophenol (0.2005 g 1.2 mmol), and pentafluoropyridine (0.3173 g. 1.9 mmol) was added to the capsule and agitated for 1 minute. No reaction. GC results: retention time (%) 7.719 min (100%).

Example 9: Cesium carbonate (0.3581 g, 1.1 mmol), allyl alcohol (0.3952 g 6.8 mmol), and pentafluoropyridine (0.1949 g. 1.2 mmol) was added to the capsule and agitated for 1 minute. GC results: retention time (%) 1.649 min (11.5%) Allyl-OH, 1.832 min (10.6%) PFP, 5.456 min (39.6%) mono adduct.

Example 10: Cesium carbonate (0.3629 g, 1.1 mmol), Krytox® methylene alcohol (1.0000 g, 0.5 mmol), and pentafluoropyridine (0.3640 g. 2.2 mmol) was added to the capsule and agitated for 1.5 minutes. GC results: retention time (%) 5.452-8.673 min (10.6%) HEC, 8.967-11.942 min (89.4%) Krytox® $CH_2OC_5F_4N$.

Example 11: Cesium carbonate (0.3650 g, 1.1 mmol), Eugenol (0.1764 g, 1.1 mmol), and pentafluoropyridine (0.7790 g. 4.6 mmol) was added to the capsule and agitated for 1 minute. GC results: retention time (%) 10.752 min (100%) mono-adduct.

Example 12: Cesium carbonate (0.3600 g, 1.1 mmol), MACH I (1.0500 g, 1.0 mmol), and pentafluoropyridine (0.3700 g. 2.2 mmol) was added to the capsule and agitated for 1 minute. GC results: retention time (%) 2.158-6.715 min (4%) HEC, 7.347-9.758 min (16.6%) mono-, 10.765-12.346 (77.3%) di-adduct, 13.390-16.289 min (6.1%) cross-linked.

Example 13: Cesium carbonate (0.3500 g, 1.1 mmol), Eugenol (0.1886 g, 1.1 mmol), and pentafluoropyridine (0.0577 g. 0.3 mmol) was added to the capsule and agitated for 1 minute. GC results: retention time (%) 8.320 min (37.5%) Eugenol, 10.768 min (10.3%) mono, 16.416 (52.2%) di. 19F-NMR results: 16% mono-, 80.8% di-, and 3.2% tri-adduct.

Example 14: Cesium carbonate (0.3700 g, 1.1 mmol), Eugenol (0.1827 g, 1.1 mmol), and pentafluoropyridine (0.0616 g. 0.4 mmol) was added to the capsule and agitated for 5 minutes. GC results: retention time (%) 8.292 min (21.3%) Eugenol, 16.416 (78.7%) di. 19F-NMR results: 17% di-, and 83% tri-adduct.

Example 15: Cesium carbonate (0.3700 g, 1.1 mmol), Eugenol (0.1438 g, 0.9 mmol), and pentafluoropyridine (0.0503 g. 0.3 mmol) was added to the capsule and agitated for 1 minute. GC results: retention time (%) 8.317 min (9.2%) Eugenol, 16.414 (90.8%) di. 19F-NMR results: 18.6% di-, and 81.4% tri-adduct.

Example 16: This is a comparative example. Potassium fluoride (0.1800 g, 3.1 mmol), Eugenol (0.5000 g, 3.0 mmol), and pentafluoropyridine (0.1500 g. 0.9 mmol) was added to the capsule and agitated for 1 minute. No reaction. GC results: retention time (%) 8.292 min (100%) Eugenol. 19F-NMR results: 100% PFP.

Example 17: This is a comparative example. Cesium carbonate (0.3663 g, 1.1 mmol), Eugenol (0.1931 g, 1.2 mmol), and hexafluorobenzene (0.4022 g, 2.2 mmol) was added to the capsule and agitated for 1 minute. No reaction. GC results: retention time (%) 8.320 min (93.6) Eugenol, 10.707 min (6.4%) mono. 19F-NMR results: 100% PFP.

Example 18: Cesium carbonate (0.3517 g, 1.1 mmol), Fluorolink E10H (1.0046 g, 1.0 mmol), and pentafluoropyridine (0.3729 g. 2.2 mmol) was added to the capsule and agitated for 1 minute. 19F-NMR results: 70.3% di and 29.7% mono.

Example 19: A fluoropolymeric system was made as follows: Cesium carbonate (0.3517 g, 1.1 mmol), Fluorolink E10H (1.0046 g, 0.56 mmol), and pentafluoropyridine (0.3729 g. 2.2 mmol) was added to the capsule and agitated for 1 minute. 19F-NMR results: 70.3% di and 29.7% mono. The fluoropolymeric system is used as a lubricant additive by adding the fluoropolymeric system to a lubricant. The fluoropolymeric system is also used as a lithium battery additive by adding the fluoropolymeric system to a lithium battery wherein serves as electrolyte. The fluoropolymeric system is also used as a viscosity modifier by adding the fluoropolymeric system to an oil. The fluoropolymeric system is also used as an anticorrosive intermediate by adding the fluoropolymeric system to a lubricant which is applied to a metal.

The fluoropolymeric system of Example 19 is used as a lubricant additive by adding the fluoropolymeric system to a lubricant.

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While the present invention has been illustrated by a description of one or more embodiments thereof and while these embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the scope of the general inventive concept.

What is claimed is:

1. A process of making a monomer having the following formula:

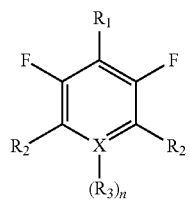

wherein
  a) $R_1$ is a branched unsubstituted hydrocarbon, unbranched unsubstituted hydrocarbon, branched substituted hydrocarbon or unbranched substituted hydrocarbon;
  b) each $R_2$ is independently fluorine, a branched unsubstituted hydrocarbon, branched unsubstituted hydrocarbon, branched substituted hydrocarbon or unbranched substituted hydrocarbon;
  c) X is carbon and the indice n is 1; and
  d) $R_3$ is fluorine said process comprising combining a nucleophile, a carbonate and a fluoro-substituted aromatic in a mill to form a combined composition or combining a nucleophile, a carbonate and a fluoro-substituted aromatic to form a combined composition; and milling said combined composition.

2. The process according to claim 1, wherein:
  a) said nucleophile is selected from the group consisting of a tetrel, a pnictogen, a chalcogen and mixtures thereof;
  b) said carbonate is selected from the group consisting of potassium carbonate and cesium carbonate; and
  c) said fluoro-substituted aromatic material is selected from the group consisting of a fluoro-substituted aromatic molecule, a polymer comprising a fluoro-substituted aromatic moiety and mixtures thereof.

3. The process according to claim 1, wherein said milling is conducted using a ball mill, a planetary ball mill, vibration ball mill, a stirring ball mill, a pin ball mill, a rolling ball mill, or an auger mill.

4. A process of making a polymer network said process comprising combining a nucleophile and a monomer having the following formula:

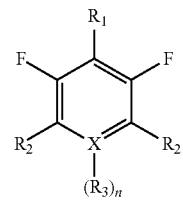

wherein
  a) $R_1$ is a branched unsubstituted hydrocarbon, unbranched unsubstituted hydrocarbon, branched substituted hydrocarbon or unbranched substituted hydrocarbon;
  b) each $R_2$ is independently fluorine, a branched unsubstituted hydrocarbon, branched unsubstituted hydrocarbon, branched substituted hydrocarbon or unbranched substituted hydrocarbon;
  c) X is carbon and the indice n is 1; and
  d) $R_3$ is fluorine
in a mill to form a combined composition or combining a nucleophile and said monomer to form a combined composition and then placing said combined composition in a mill; and milling the said combined composition.

5. The process of claim 3 wherein nucleophile is selected from the group consisting of nucleophile is selected from the group consisting of a tetrel, a pnictogen, a chalcogen and mixtures thereof.

6. The process of claim 4 wherein a second monomer, other than a monomer having the following formula:

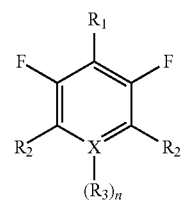

wherein
- a) $R_1$ is a branched unsubstituted hydrocarbon, unbranched unsubstituted hydrocarbon, branched substituted hydrocarbon or unbranched substituted hydrocarbon;
- b) each $R_2$ is independently fluorine, a branched unsubstituted hydrocarbon, branched unsubstituted hydrocarbon, branched substituted hydrocarbon or unbranched substituted hydrocarbon;
- c) X is carbon and the indice n is 1; and
- d) $R_3$ is fluorine, is added to said ball mill during said process.

7. The process of claim 6 wherein, said second monomer is added after said combined composition is formed.

\* \* \* \* \*